United States Patent [19]

Johnson

[11] 4,165,748
[45] Aug. 28, 1979

[54] CATHETER TUBE HOLDER

[76] Inventor: Melissa C. Johnson, 758 Main St., Leominster, Mass. 01453

[21] Appl. No.: 849,080

[22] Filed: Nov. 7, 1977

[51] Int. Cl.² .............................................. A61M 25/02
[52] U.S. Cl. ........................... 128/348; 128/DIG. 26; 128/133; 248/205 A; 246/7 AR; 24/DIG. 11
[58] Field of Search .......... 128/349 R, 133, DIG. 26, 128/346, 348; 24/67 AR, DIG. 18, DIG. 11; 248/205 A

[56] References Cited

U.S. PATENT DOCUMENTS

| 3,160,158 | 12/1964 | Rayhart | 128/DIG. 26 |
| 3,288,136 | 11/1966 | Lund | 128/DIG. 26 |
| 3,430,300 | 3/1969 | Doan | 128/349 X |
| 3,677,250 | 7/1972 | Thomas | 128/348 |
| 3,726,280 | 4/1973 | Lacount | 128/349 R |
| 3,765,421 | 10/1973 | Poprik | 128/349 R |
| 3,782,383 | 1/1974 | Thompson et al. | 128/214 |
| 3,826,254 | 7/1974 | Mellor | 128/DIG. 26 |
| 3,834,380 | 10/1974 | Boyd | 128/DIG. 26 |
| 3,878,849 | 4/1975 | Muller | 128/349 R |
| 3,990,454 | 11/1976 | Schlesinger | 128/349 R |

Primary Examiner—E. H. Eickholt
Attorney, Agent, or Firm—Charles R. Fay

[57] ABSTRACT

A simple easily applied one-piece catheter tube holder originally made flat and comprising two main parts having adhesive thereon for temporary attachment to the limb of the patient, there being a narrow bridge also provided with adhesive and connecting the two main parts, said narrow bridge being foldable in the center thereof to form a doubled member, and having fasteners such as snap fasteners or Velcro for holding the same in position to releasably hold the catheter tube in the desired orientation to the patient.

4 Claims, 3 Drawing Figures

CATHETER TUBE HOLDER

BACKGROUND OF THE INVENTION

There have been proposals made for catheter tube holders to attach to the leg or thigh but in all cases they have been expensive, difficult to apply or largely ineffective, and the usual manner of holding a catheter tube is simply by strapping it with adhesive bandage to the thigh of the patient, so that the adhesive seal is broken to remove the catheter. This is considered to be a poor practice as the tube is not often correctly orientated and an excess of adhesive bandaging material is utilized especially where the practitioner completely encircles the thigh of the patient in order to hold the tube where desired.

SUMMARY OF THE INVENTION

In the present case the catheter tube holder comprises a pair of relatively large spaced main members having adhesive thereon normally covered by a protective tear off strip or sheet, said members being connected by a narrow bridge also having adhesive thereon to secure the bridge parts in doubled over form when the two main members are placed substantially together on the body of the patient. When the device is applied to the patient, the tube is positioned adjacent the bridge which is bent around the tube, the bridge parts having fasteners such as snap fasteners, or Velcro, etc., to secure the tube, and in this way a very simple and inexpensive holder is provided which is quickly and easily applied in correct orientation and which is as easily removed.

It is preferred that the entire holder be died out in a single piece of material and this enhances the inexpensiveness of the device.

PREFERRED EMBODIMENT OF THE INVENTION

Figure 1:
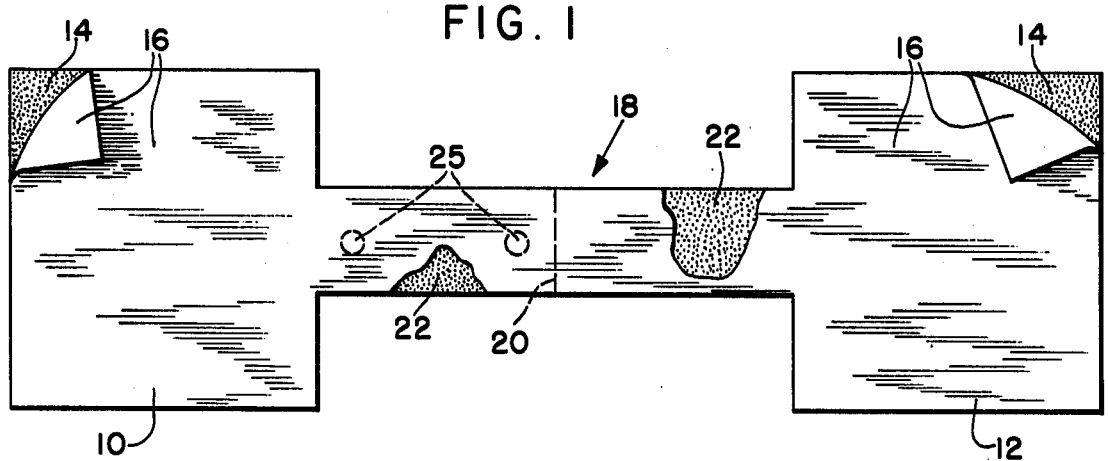
FIG. 1 is a bottom plan view, showing the device flat.

As shown in FIG. 1, the catheter tube holder in the present invention is a died out single piece which comprises a pair of main members 10 and 12 each of which is preferably supplied with pressure sensitive adhesive 14,14 on one surface thereof, being originally covered by a tear off protective sheet such as at 16,16. The two main members 10 and 12 are separated by a narrow bridge generally indicated at 18 having a hold area 20 midway of the ends thereof and having adhesive material, etc., 22,22 thereon. The adhesive 22,22 is also provided with the tear off covering material and this may be integral with that at portions 16 thereof that cover the main members 10 and 12.

One side only of the bridge is provided with complementary fasteners, e.g. snap fasteners, Velcro, etc., as at 25, on the nonadhesive side of the bridge.

Figure 2:
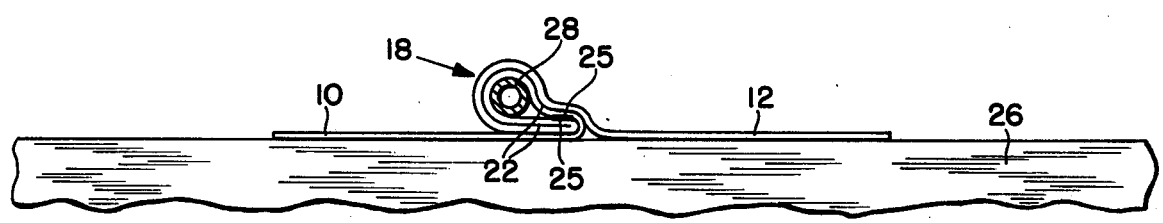
FIG. 2 is a side elevation illustrating the device in operative position.
Figure 3:
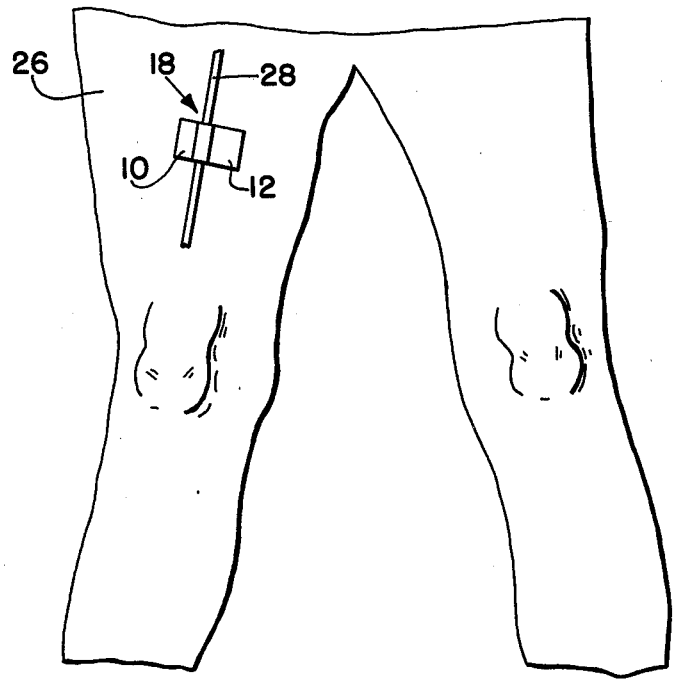
FIG. 3 is a plan view showing the device is applied to the patient.

In FIGS. 2 and 3, the patients's limb is indicated at 26, and in the operation of the device the main members 10 and 12 are adhesively secured thereto in generally close association thereof, with the bridge 18 folded. The adhesive areas at 22 adhere together and make a doubled, free-ended member.

The fasteners 25 may comprise pressure sensitive adhesive, Velcro, or any other such material, but they may also be in the form of mechanical fasteners of the type shown at 25. These represent snap fasteners which cooperate to hold the bridge in the FIG. 2 position, forming a loop including the tube 28.

The tube 28 is therefore easily held in desired position and can be removed by undoing fasteners 25, of whatever nature, so that breaking the adhesive seal of prior art devices is not necessary.

I claim:
1. A catheter holder comprising a pair of main members adapted to be secured to the limb of a patient in closely spaced relation,
    a piece of material extending from corresponding edges of each of said main members,
    said pieces of material being the same in size and having a width less than the width or length of the main members,
    said extending pieces being secured together in superposed relation forming a double bridge member,
    and cooperating fastening means on the combined pieces at one side thereof, said fastening means being located at the base of said bridge member adjacent to the corresponding closely spaced edges of the main members, and adjacent the end portion of said bridge member, so that when the fastening means are connected, a separable loop is provided to include and hold a catheter in desired orientation with respect to the patient.
2. The tube holder of claim 1 wherein the main members are provided with adhesive material for temporary securement to the body of the patient.
3. The tube holder of claim 1 including adhesive material on the pieces to form the double bridge member.
4. The tube holder of claim 1 wherein said fastening means is Velcro.

* * * * *